United States Patent [19]
Nguyen

[11] Patent Number: 4,482,708
[45] Date of Patent: Nov. 13, 1984

[54] 3', 5'-DINUCLEOSIDE PHOSPHATES OF 5,6-DICHLORO-1-β-D-RIBOFURANOSYL-1-BENZIMIDAZOLE AND METHODS OF MAKING AND USING THE SAME

[76] Inventor: Nicolas C. Nguyen, 360 E. 72nd St., New York, N.Y. 10021

[21] Appl. No.: 406,458

[22] Filed: Aug. 9, 1982

[51] Int. Cl.$^3$ .................... C07H 15/12; C12P 21/00
[52] U.S. Cl. .................... 536/28; 435/811; 435/68; 424/180
[58] Field of Search .............. 536/28; 424/180; 435/811, 68

[56] References Cited
U.S. PATENT DOCUMENTS 3,764,594  10/1973  Roldan et al. .................... 536/28
4,378,458  3/1983   Gohlke et al. .................... 536/28

FOREIGN PATENT DOCUMENTS 0064796  11/1982  European Pat. Off. .............. 536/28

Primary Examiner—Alan Siegel

[57] ABSTRACT

A new 3',5'-dinucleoside phosphate, the pharmaceutically acceptable salts thereof and intermediates therefor. The 3',5'-dinucleoside phosphate of 5,6-dichloro-1-β-D-ribofuranosyl-1-benzimidazole and namely 5,6-dichloro-1-β-D-ribofuranosyl-1-benzimidazole-3'-yl-5,6-dichloro-1-β-D-ribofuranosyl-1-benzimidazole-5'-yl-phosphate possesses potent inducing activity for the cellular synthesis of interferons and in particular β-interferon. The compound is also markedly effective to induce antiviral levels of interferon and possesses significant interferon potentiation properties. The invention also contemplates methods for the preparation of the new compounds and for using the new 3',5'-dinucleoside phosphate.

2 Claims, No Drawings

3',5'-DINUCLEOSIDE PHOSPHATES OF 5,6-DICHLORO-1-β-D-RIBOFURANOSYL-1-BENZIMIDAZOLE AND METHODS OF MAKING AND USING THE SAME

The present invention relates to a new compound, i.e., 3',5'-dinucleoside phosphate of dichloro-5,6-β-D-ribofuranosyl-1-benzimidazole as well as the salts thereof, intermediates therefor, processes for the preparation of these compounds, interferon inducing agents containing the 3',5'-dinucleoside phosphate of dichloro-5,6-β-D-ribofuranosyl-1-benzimidazole and methods for using these compounds.

Despite efforts made heretofore to discover drugs that may be of value in the systemic treatment of viral infections, such infections have been singularly resistant to chemotherapy, except for those caused by certain of the large viruses which are treated by a number of antibiotics and sulfonamides. The intracellular intimate relationship to nuclear metabolism of viral replication makes it difficult to destroy a virus without irreparable damage also to the host cell. Nevertheless, research on virustatic and virucidal drugs has continued. There has been in this connection a continuing strong interest in "interferon." An interferon has been defined as a proteinaceous substance produced by mammalian cells in response to active or inactive viruses or even certain bacteria which enables cells to become refractory to infection by the same viruses or to other viruses which are not necessarily serologically related. In addition to viruses, the interferons have been found to inhibit plasmodia, toxoplasmae and chlamydiae and the growth of certain human malignant tumors.

It is known that the production of interferon can be stimulated by a great number of viruses and especially by RNA and DNA containing viruses and also by a wide variety of unrelated synthetic and naturally occurring substances derived from bacteria, rickettsiae, yeast, fungi and plants and by double or multistandard RNA as well as by certain synthetic substances as hereinafter set out.

Unfortunately, the toxicity of interferon inducing substances limit substantially their in vivo uses. Consequently, there is great interest in substances which can stimulate the in vivo production of interferons in inhibiting ranges without concomitant side effects.

The novel compound of the invention is 5,6-dichloro-1-β-D-ribofuranosyl-1-benzimidazole-3'-yl-5,6-dichloro-1-β-D-ribofuranosyl-1-benzimidazole-5'-yl-phosphate and results from a dimerization of 5,6-dichloro-1-β-D-ribofuranosyl benzamidazole. According to the present invention, the novel compound has the formula [15]

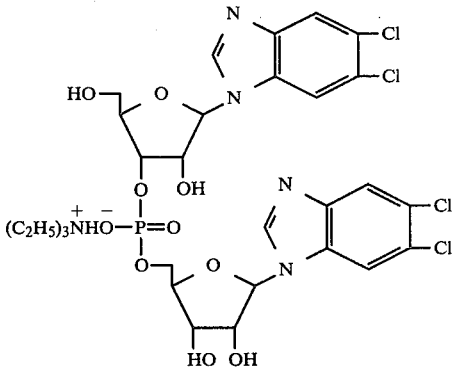

The above dimer is possessed of unique interferon inducing and potentiating properties not found to be associated with the monomer. The invention also contemplates the intermediates used in the preparation of this compound and the effective agents characterized by a content thereof.

The monomer starting material used in this invention, i.e., 5,6-dichloro-1-β-D-ribofuranosyl benzamidazole (hereinafter "DRB") [1] and its synthetic has been described by Kisman et al in the J. Amer. Chem. Soc. 79, 1185 (1957).

The novel compound 5,6-dichloro-1-β-D-ribofuranosyl-1-benzimidazole-3'-yl-5,6-dichloro-1-β-D-ribofuranosyl-1-benzimidazole-5'-yl-phosphate as described and claimed herein (hereinafter "DDB"), the intermediates therefor and the process for its production can be illustrated by the following planned sequence:

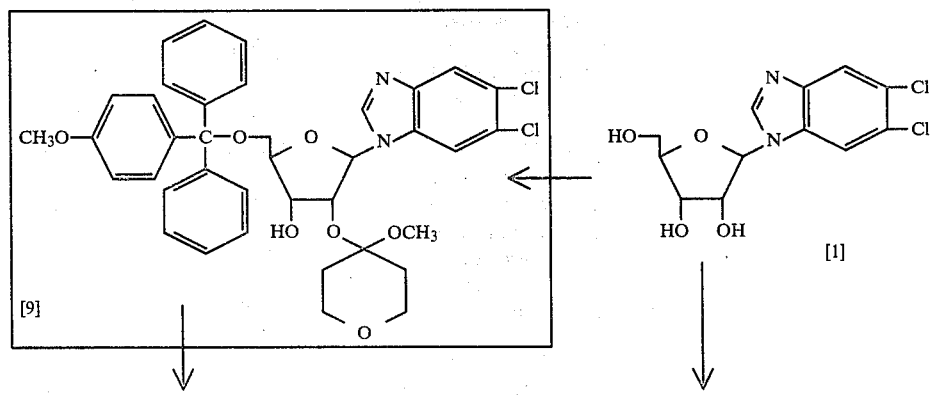

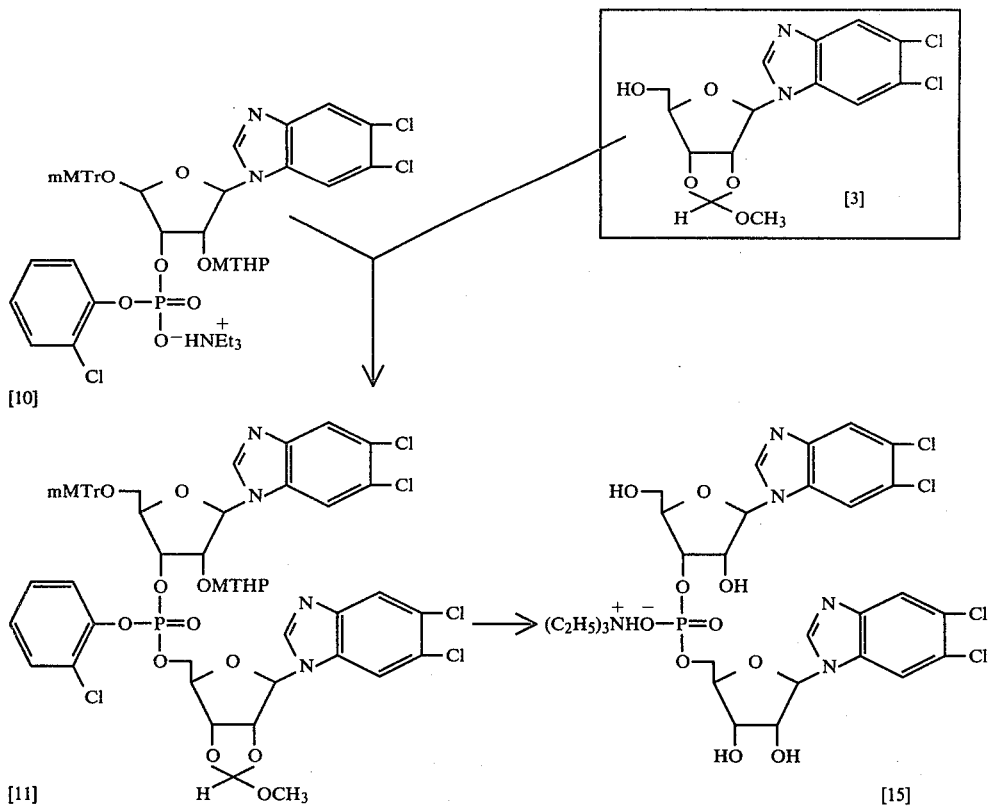

The monomer DRB has been reported by Tamm et al, J. Exp. Med., 99, 127 (1954) to inhibit influenza virus replication in ovo and in mice. The work was contradicted by subsequent studies of Kisman et al, J. Am. Chem. Soc. 79, 1185 (1957) which established that DRB does not inhibit the multiplication of the influenza virus in mice and that furthermore it is inactive against a variety of other viruses in ovo, in tissue culture and in mice. DRB has also been reported to be useful in the superinduction of human fibroblast cell cultures to produce β-interferon (Sehgal et al, Science, 190, 282 (1975), Sehgal et al, Virology, 89, 186 (1978) and Stewart et al, J. Gen. Virology 37, 221 (1977)).

According to Sehgal et al (Science 190, 282 (1975), polyinosinic-polycytidylic acid [poly(I-C)] induced the production of β-interferon by a culture of human diploid fibroblasts, measured between 5 and 24 hours from induction. The influence of the DRB in the production of β-interferon was monitored and a close correlation between the superinducing effect of DRB and inhibition of RNA synthesis was observed. Cultures that contained DRB were found to continue to produce interferon for up to four days. Removal of the DRB at any time during this period resulted in a prompt and complete termination of interferon production.

DRB however is toxic to the cells in the culture. The repeated induction of interferon using DRB cannot be carried out for more than four days without massive destruction of the cells taking place in the culture.

In U.S. Pat. No. 3,300,478 there are described arabinofuranosyl 2',5'- and 3',5'-dinucleoside phosphates and that these dimers exhibit significant cytostatic activity in vitro particularly against KB tumor cells and against certain viruses, such activity not being observed in the corresponding known monomers. The unexpected activity for the dimer was construed to be a significant advance in the art and meritorious of patent protection.

According to the invention, the new compound 5,6-dichloro-1-β-D-ribofuranosyl-1-benzimidazole-3'-yl-5,6-dichloro-1-β-D-ribofuranosyl-1-benzimidazole-5'-yl-phosphate, i.e., the dimer (DDB), and its intermediates are synthesized from the starting compound 5,6-dichloro-1-β-D-ribofuranosyl benzamidazole (DRB).

The dinucleoside phosphate, i.e., 5,6-dichloro-1-β-D-ribofuranosyl-1-benzimidazole-3'-yl-5,6-dichloro-1-β-D-ribofuranosyl-1-benzimidazole-5'-yl-phosphate and its synthesis from 5,6-dichloro-1-β-D-ribofuranosyl benzamidazole (DRB) involves:

1. Protecting the 2' position in Synthon B [9] in order to avoid migration of the phosphate moiety from the 3'- to the 2'-position in the last step of the unblocking.

2. Protecting group R$_2$ of Synthon B [9] must not be of the reacting type (acetyl or benzoyl, neither labile nor silyle base) in order to avoid its isomerization.

3. The group R$_1$ must be selective for a primary hydroxyl group.

4. Synthon A [3] must be protected in the 2'- and 3'-positions in order that the phosphodiester bond can be specifically introduced into the 3'- and 5'-positions of the two nucleosidic moieties.

The novel nucleoside compound can be converted into its pharmaceutically acceptable salts in the conventional manner as for instance by treatment of the free base with a mineral acid, such as hydrochloride acid, hydrobromic acid and the like.

The new nucleoside phosphate of the invention has been evaluated as an inducing agent for producing β-interferon and as an antiviral agent and the results obtained compared to those produced by using the monomer DRB under substantially identical conditions. It was established that the dimer was some 3–4 fold (on the average) more effective than the corresponding monomer.

When tested as an inducing agent for the production of β-interferon by diploid cell culture, the dimer produced results which are dramatically different not only in their cytotoxicity (DRB is much more toxic) but also in the amount of the β-interferon produced.

When tested as an antiviral agent, the use of the dimer produced marked virustatic and virucidal activity as compared to the monomer.

When tested as a potentiating agent for β-interferon, the dimer produced significantly enhanced effects in the treatment of viral infections as compared to the use of the combination of monomer and β-interferon.

I. The synthesis of the novel final compound (DDB), the novel intermediates and the process of the production thereof are described in the following sequence of steps. The preparations as hereinafter set out are illustrative of the products and process of the present invention but are not to be construed as limiting.

(A) Synthesis of Synthon A [3]

The group for protecting positions 2'- and 3'- which is used herein is o-methoxy methylidene and can be introduced in one step. It allows for the simultaneous protection of the hydroxyl groups in the 2'- and 3'-positions, and can thereafter be easily removed in the final unblocking:

A process of preparing Synthon A [3] is described immediately below:

A suspension of the nucleoside [1] (1 g=3.13 mmoles) and p-toluene monohydrate sulfonic acid (0.076 g=0.4 mmole) in 3.8 ml of trimethyl-orthoformate is shaken at ambient temperature for 48 hours. A thin layer chromatography (TLC) (eluent I) shows essentially two stains corresponding to compounds [2] and [3].

The reaction mixture is neutralized by using a solution of sodium methylate (2M in methanol, filtered and then coevaporated with chloroform.

After solubilization in chloroform has taken place, activated silica is added and the reaction mixture is shaken at ambient temperature until a complete transformation of compound [2] into Synthon A [3] has taken place, as confirmed by TLC (duration 7 days).

Following filtration, the silica is thoroughly rinsed with chloroform, then with methanol, the filtrates are pooled, evaporated to dryness and chromatographed on a silica gel column (eluent II). Synthon A is obtained and crystallized (0.87 g) from a mixture of CHCl₃/diisopropylether (yield: 77%):

o-methoxymethylene-2',3'-β-D-ribofuranosyl-1-dichloro-5,6-benzimidazole [3] (Synthon A)

$C_{14}H_{14}N_2O_5Cl_2$

Molecular weight: 361.18.
Melting point: 147° C.
Mass spectrography: (temperature: source 180°, probe: 160°) 361 (41); 359 (62); 188 (38); 186 (55); 175 (100); 134 (38); 97 (31)
$^1$H nuclear magnetic resonnance (NMR)=δppm (CDCl₃)=8.18 (s,1H), 7.60 (s,1H) and 7.68 (s,1H)=H-2, H-4 and H-7; 6.14 (d, 1H=H₁; JH₁'-2'=3,OH₂); 6.05 and 5.98 (2s; 1H; H of methylidene; 2 diastereoisomers, respective ratio: 15 and 85%) 5.1 (m, 3H'=H-2', H-3', OH-5'), 4.54 (m, 1H=H-4'), 3.96 (m, 2H=H-5', H-5"), 3.47 and 3.36 (2s; 3H, OCH₃ of methylidene, two diastereoisomers).

UV Et$_{OH}$ 95: λmax. 294 mm (ε: 4100); 286 mm (ε: 4250); 254 mm (ε: 5650) εmin. 292 mm (ε: 3400); 271 mm (ε: 2350); 238 mm (ε: 3100).

(B) Synthesis of Synthon B [9]

In order to introduce the substituents R₁ and R₂, the following four step synthesis sequence is carried out:

1. simultaneous blocking of the 3'- and 5'-hydroxyl groups;
2. introduction of the R₂ substituent onto the 2'-hydroxy group;
3. concomitant unblocking of hydroxyl groups in the 3'- and 5'-positions; and
4. selective blocking of the 5'-hydroxyl group.

The procedure is conducted as now described:

Step 1

In order to simultaneously block the hydroxyl groups in the 3'- and 5'-positions of the nucleoside [1], dichloro-1,3-tetraisopropyl-1,1,3,3-disiloxane [4] is used:

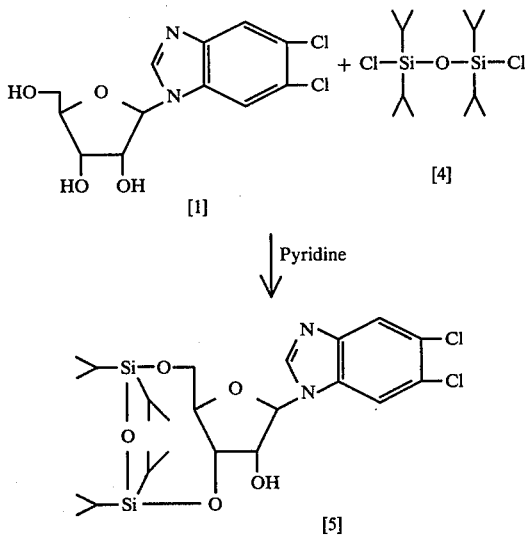

To a solution of nucleoside [1] (2 g=6.27 mmoles) in 18.6 ml of anhydrous pyridine, there is added reagent [4] (2.51 g=6.83 mmoles). The reaction solution is left overnight on a shaker at ambient temperature and protected from humidity.

A TLC (thin layer chromatography) with eluent I and III, shows the presence of a new stain corresponding to compound [5].

Following filtration and dilution with CHCl₃, the solution obtained is washed first with a saturated solution of sodium bicarbonate, and then with water. The organic phases are pooled and dried on sodium sulfate. Chromatography is carried out on a silica gel column (eluent IV) and results in there being obtained 2.9 g of compound [5] in the form of a foam. This compound is sufficiently pure to be utilized in the next step:

o-(tetraisopropyldisiloxane-1,3-diyl)-3'5'-β-D-ribofuranosyl-1-dichloro-5,6-benzimidazole [5]

$C_{24}H_{38}N_2O_5Cl_2Si_2$

Molecular weight: 561.32.
H-NMR, δppm (CDCl₃)=8.21 (s,1H), 7.89 (s,1H) and 7.60 (s,1H)=H-2, H-4 and H-7; 5.86 (s,1H=H1');

4.7–4.0 (m, 5H=H-2′,H-3′,H-4′,H-5′, H-5″), 2.9 (ss, 1H=OH-2′); 1.00, 1.06 and 1.11 (28H=Si-isopropyl).

Step 2

The reagent used to block position 2′- is monomethoxytetrahydropyranynne:

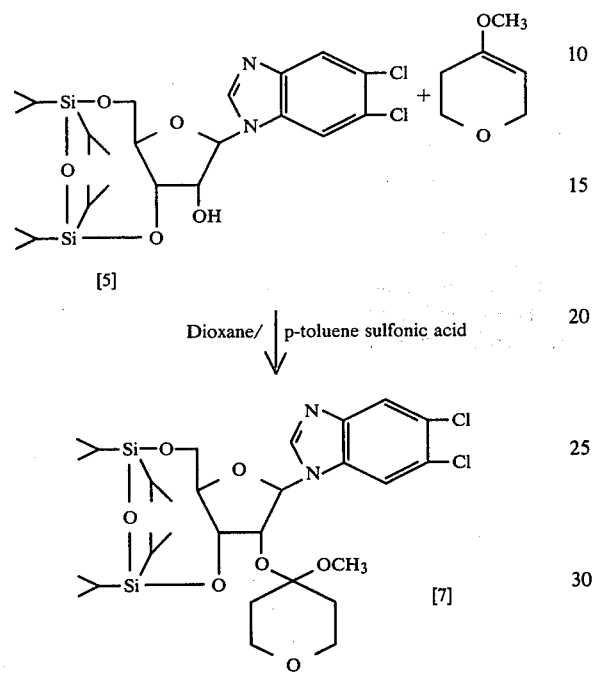

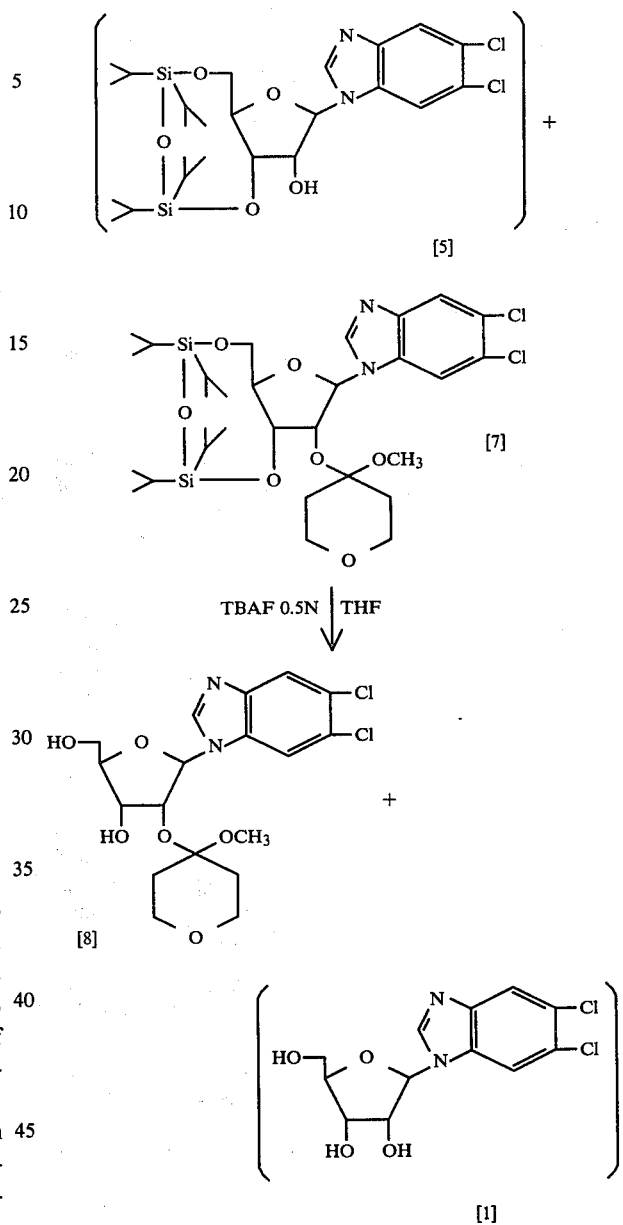

To a solution of nucleoside [5] (2.07 g=3.68 mmoles) and paratoluene monohydrate sulfonic acid (0.36 g=0.19 mmole) in 20 ml of dioxane, there is added methoxy-4-dihydro-5,6 2-H-pyranne [6] (2.75 g=24.12 mmoles=4.8 ml). The reaction mixture is shaken for 18 hours at ambient temperature. A second portion of reagent [6] (1.0 g) is then added and the shaking continued for a further 6 hour period.

The reaction mixture is thereafter neutralized with $NH_4OH$, diluted with water, concentrated under reduced pressure, redissolved in $CHCl_3$ and washed successively with a saturated solution of sodium bicarbonate and water.

The organic phases are then pooled, dried on sodium sulfate, filtered and evaporated to dryness.

A TLC (eluent V) shows essentially the presence of the desired compound [7] and some of the starting compound [5]. Chromatography using a column (eluent VI) results in the collection of 1.26 g of compound [7] in pure form ($C_{30}H_{48}N_2O_7Cl_2Si_2$; molecular weight: 561.38), and 1.0 g of a mixture of compounds [5] and [7]. These two fractions are reserved and used separately in the following step:

Step 3

The simultaneous desilylation of the hydroxyl groups in the 3′- and 5′-positions is accomplished with tetrabutylammonium fluoride (TBAF) in anhydrous tetrahydrofuran (THF):

This step proceeds as hereinafter:

1.26 g. of compound [7] is dissolved in 11.2 ml of a solution of 0.5N of TBAF in THF.

After 4 hours on the shaker, at ambient temperature, the solution is diluted with 50 ml of a mixture of pyridine-methanol-water (3:2:2, vol/vol) and treated with 6 ml of Dowex resin 50 w, under the form of pyridinium. The resin is then filtered, washed with water and methanol. The filtrates are pooled, evaporated to dryness and coevaporated successively with pyridine and toluene. Chromatography performed on a silica gel column (eluent II) results in the recovery of 0.68 g of compound [8]:

o-methoxytetrahydropyrannyl-2′-β-D-ribofuranosyl-1-dichloro-5,6-benzimidazole [8]

$C_{18}H_{22}O_6N_2Cl_2$

Molecular weight: 433.29.

Melting point: 175° C. (crystallization $CHCl_3/CCl_4$).

Mass spectrography (temperature: source 180°, probe: 200°) 433 (17); 431 (22); 331 (8); 329 (11); 320 (10); 318 (13); 219 (15); 218 (12); 217 (55); 216 (18); 215 (100); 189 (16); 188 (18); 187 (21); 186 (24); 115 (>100).

$^1$H Nuclear magnetic resonnance (NMR): δppm (DMSO-d$_6$): 8.64 (s,1H), 8.45 (s,1H), 7.96(s, 1H)=H-2, H-4 and H-7; 6.06 (d, 1H=N-s'; J$_{1'-2'}$=7.08 Hz), 5.38 (t, 1H=OH-5'; J$_{OH-5',H5'-5'}$=5.1 Hz), 5.26 (d, 1H=OH-2'; J$_{OH-2',H-2'}$=4.2 Hz), 4.64 (m, 1H=H-2'), 4.12 (m, 2H=H-3',H-4'), 3.9–3.0 (m, 6H=H-5',H-5" and 4H of tetrahydropyrannyl), 2.36 (s, 3H=OCH$_3$), 2.0–1.2 (m, 4H=H of tetrahydropyrannyl).

Step 4

The introduction of the group R$_1$ into position 5' requires the utilization of a selective reagent for the primary hydroxyl, in order to avoid an interfering reaction on the free hydroxyl in the 3'-position. The reagent used in this instance is monometroxytrityl chloride (ClmMTr). Synthon B [9] is obtained by using as solvent dichloromethane and as a catalyst for the reaction a mixture of dimethylaminopyridine (DMAF) and triethylamine:

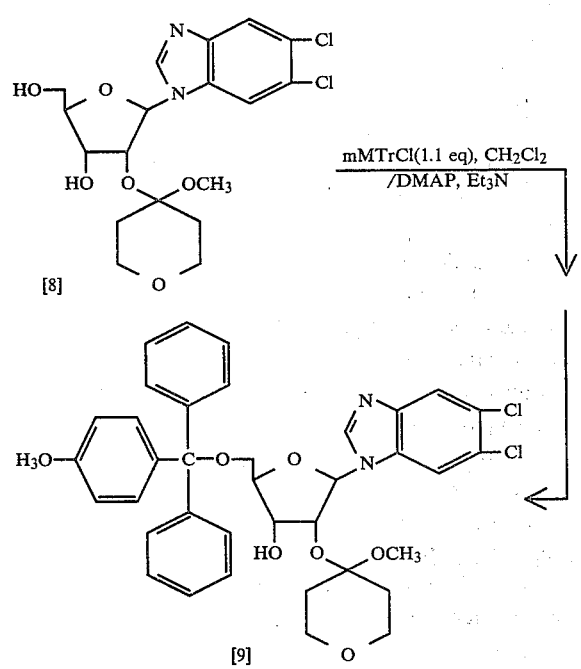

The process as carried out follows:

A solution of compound [8] (0.38 g=0.88 mmole), monomethoxytrityl chloride (0.297 g=0.96 mmole=1.1 equivalent), triethylamine (0.097 g=1.1 eq.) and dimethylaminopyridine (0.0043 g=0.04 eq.) in 9.5 ml of anhydrous dichloromethane is shaken for 20 hours, while shielded from light and humidity.

A TLC (eluent VII) shows that the reaction is practically complete. After addition of 8 ml of ice cold water, the reaction mixture is extracted twice with 30 ml of dichloromethane. The organic phase are dried on sodium sulfate, filtered and evaporated under reduced pressure.

The residue is passed through a silica chromatographic column (eluent VIII) and the compound [9] which is collected is precipitated in petroleum ether (0.45 g; yield: 73%):

o-monomethoxytrityl-5'-o-methoxytetrahydropyrannyl-2'-β-D-ribofuranoyl-1-dichloro-5,6-benzimidazole (Compound [9])

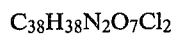

Molecular weight: 705.61.

Melting point: 114° C.–115° C.

$^1$H Nuclear magnetic resonnance (NMR), δppm (DMSO-d$_6$)=8.57 (s,1H), 8.03 (s, 1H) and 7.97(s,1H); 7.6–6.7 (m, 14H: aromatic H of monomethoxytrityl) 6.08 (d, 1H=H-1'; J$_{1-2'}$=7.2H$_2$) 5.30 (d, 1H=OH=3'; J$_{OH-3', H3'}$=4.8H$_2$) 4.78 (m, 1H=H 2'), 4.15 (m, 2H=H 3' and H-4'), 3.73 (s, 3H=OCH$_3$ of monomethoxytrityl), 3.9–3.0 (m, 6H=H5', H-5" and 4H of tetrahydropyrannyl), 2.57 (s, 3H=OCH$_3$ of tetrahydropyrannyl) 2.0–1.2 (m, 4H=H of tetrahydropyrannyl).

Mass spectrography: (temperature: source=180° C., probe=190° C.).

M$^+$·=701.

UV=Et$_{OH}$95; λmax: 295 nm (ε: 4200); 286 nm (ε: 4800) λmin.: 292 nm (ε: 3600); 272 nm (ε: 3900).

(C) Synthesis of the Arylphosphate-3'nucleoside (Compound [10])

The first step of the oligonucleoside synthesis consists in forming the arylphosphate-3' derivative (compound [10]) from Synthon B (compound [9]) by reacting the latter with an excess of o-chlorophenylphosphorodi-(thiazole-1,2,4-ide) in a mixture of acetonotrile-pyridine:

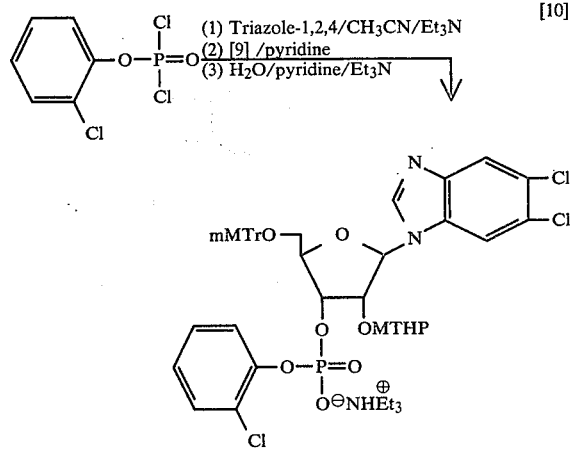

The procedure is detailed below:

A solution of o-chlorophenylphosphorodi-(triazole-1,2,4-ide) is prepared in situ in 1.24 ml of anhydrous acetonitrile, from 0.2195 g (3.224 mmoles) of triazole-1,2,4; 0.3042 g (1.24 mmoles) of o-chlorophenylphosphorodichloridate, and 0.251 g (2.48 mmoles) of triethylamine.

After 15 minutes of shaking at ambient temperature, a solution of 0.35 g (0.496 mmoles) of compound [9] in 2.48 ml of anhydrous pyridine is added and the shaking continued for a further 20 minutes.

A solution of 0.314 g (3.1 mmoles) of triethylamine and 0.145 g (8.06 mmoles) of water is added to 0.99 ml of pyridine and placed on a shaker for 15 minutes.

The reaction mixture is then poured into 65 ml of a saturated aqueous solution of sodium hydrogenocarbonate and extracted with chloroform (four times 20 ml). The chloroform phases are collected, pooled, and washed with an aqueous saturated solution of sodium hydrogencarbonate (twice 30 ml), then with water (twice 30 ml).

The organic phase is then dried on sodium sulfate, filtered and evaporated under reduced pressure, redissolved in a minimum of chloroform and coevaporated three times with toluene.

The foam obtained is redissolved in 2.5 ml of chloroform and poured drop by drop into 70 ml of petroleum ether under strong shaking. Compound [10] is obtained in the form of a precipitate which is recovered by decanting and then dried in a dryer.

This arylphosphate-3' derivative (compound [10]) is collected in the form of a triethylammonium salt (0.49 g) with a yield of 99%, and is sufficiently pure to be utilized directly in the next condensation step.

(D) Synthesis of the Totally Protected Dinucleoside (Compound [11])

This condensation step requires reacting Compound [10] having an arylphosphate moiety on the hydroxy-5' function of Synthon A (Compound [3]). The activating agent used in this step is mesitylenesulfonyl-1-nitro-3-triazole-1,2,4 (MSMT):

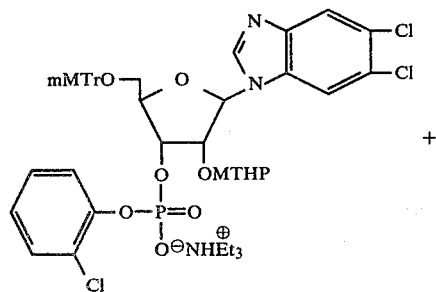

[10]

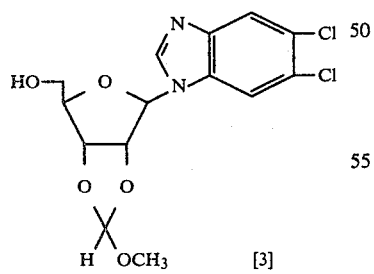

[3]

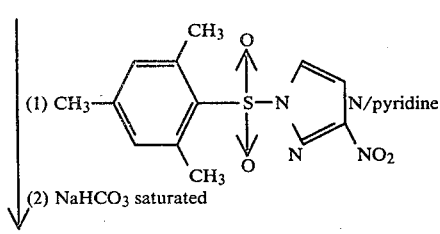

(1) CH₃—
(2) NaHCO₃ saturated

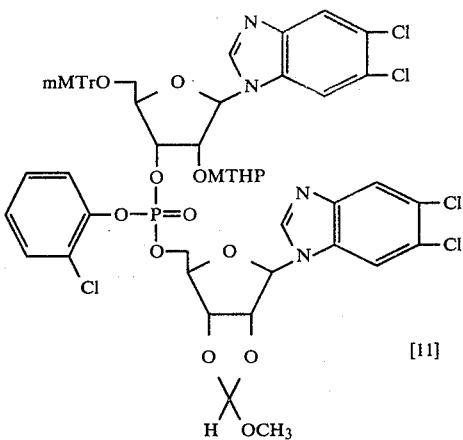

[11]

$C_{58}H_{54}N_4O_{14}Cl_5P$
Molecular weight: 1239.3

The procedure is carried out as set out immediately below:

To a solution of compound [10] (0.408 g=0.409 mmole) and of compound [3] (0.1329 g=0.368 mmole) in 2.05 ml of anhydrous pyridine, there is added MSMT (0.2978 g=1.022 mmoles) and the reaction mixture then placed on a shaker at ambient temperature. The progress of the reaction is followed on TLC (eluent VII).

The reaction is considered to be complete in 20 minutes and is stopped by the addition of 0.41 ml of a saturated aqueous solution of sodium hydrogenocarbonate. This mixture is then shaken for 15 minutes and the resulting solution then poured into a saturated solution of NaHCO₃ (60 ml). The products of the reaction are then extracted with chloroform (4 times 30 ml).

The organic phases are pooled, evaporated under reduced pressure and then coevaporated successively with toluene then chloroform.

The residue obtained is purified by silica column chromatography (eluent IX), the dinucleoside, totally protected (compound [11]) is precipitated in petroleum ether. It is collected in a yield amounting to 82% (as compared to Compound [3]).

(E) Synthesis of the Dinucleoside (Compound [15])

The dinucleoside [15], the active compound of the invention is obtained by reacting Compound [11] successively and sequentially with:

(a) tetramethylguanidinium p-nitrobenzaldoximate in order to eliminate the o-chlorophenyl group, (b) acetic acid (80%) to eliminate the monomethoxytrityle group and to transform the acetal group into a formyl-2',(3') group, and, (c) with aqueous ammonia to hydrolyze the formyl group.

The process sequence follows:

(a) Unblocking of the phosphorus:

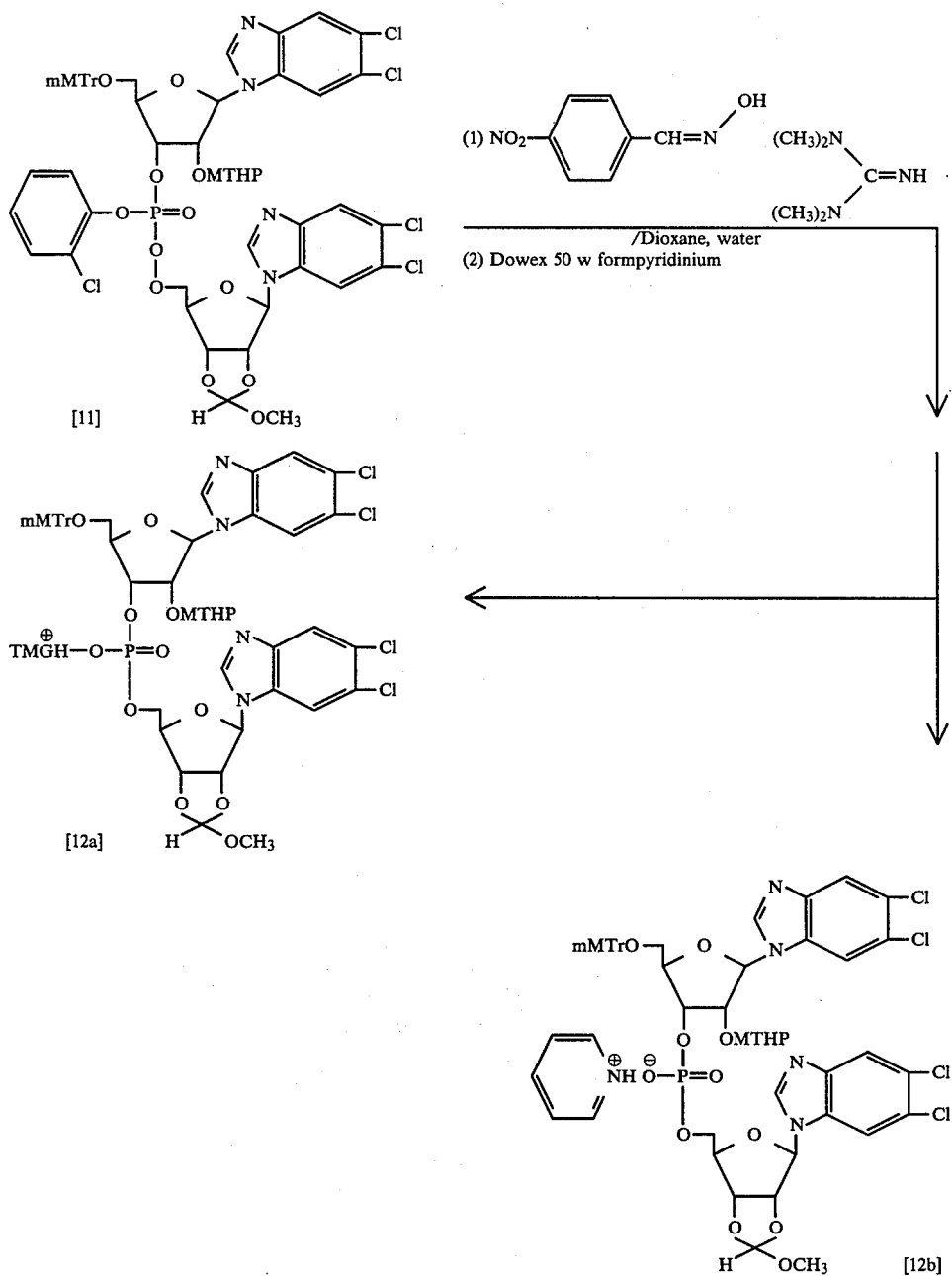

A solution of dinucleoside, totally protected compound [11] (0.340 g=0.2743 mmoles) is treated with nitro-4 synbenzaldoxime (1.592 g=9.59 mmoles) and N,N,N,N,-1,1,3,3 guanidine (TMG) (1.104 g=9.59 mmoles) in a mixture of dioxane-water (24 ml; 1/1; V/V) and the mixture is then shaken for 4 hours at ambient temperature.

At the end of the 4 hour period, TMG (0.58 g=5.03 mmoles) is added and the resulting solution is shaken for an additional 16 hour period.

The reaction mixture, which contains the dinucleoside [12a] in the form of a tetramethylguanidinium salt is chromatographed on a column of Dowex 50 resin form pyridinium (eluent:water/dioxane, 50/50, V/V). The eluate so collected is evaporated then coevaporated with water. The residue obtained, containing the dinucleoside [12b], in the form of a pyridinium salt, is utilized directly in the next step.

(b) Unblocking of monomethoxytrityle, methoxytetrahydropyrannyl and acetal:

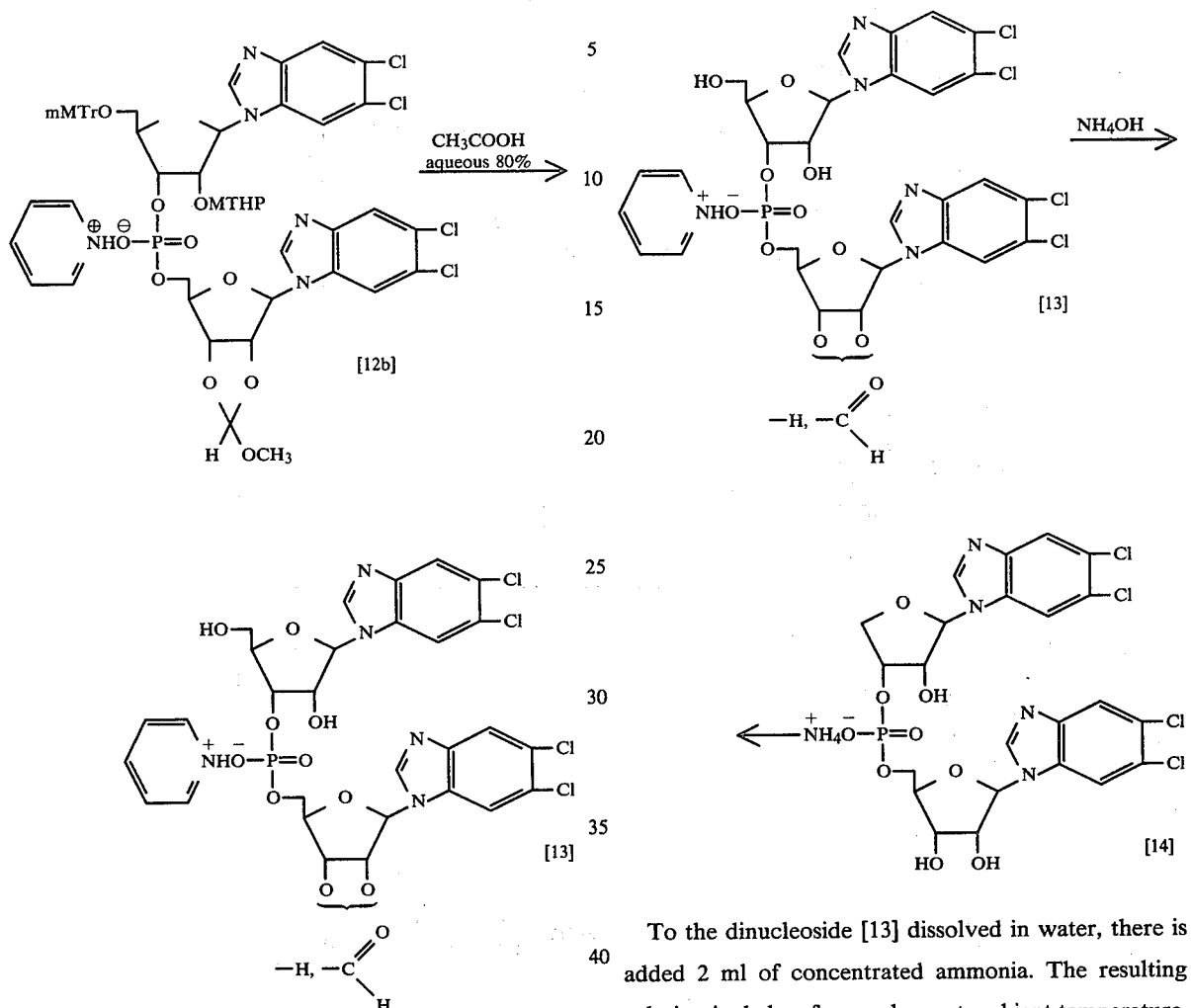

The residue obtained from the preceding step is dissolved in 50 ml of aqueous acetic acid, and the solution is left on a shaker at ambient temperature for 5 hours.

After dilution with water, the solution is washed with chloroform (15 times 50 ml) to eliminate all of the secondary products resulting from the last two steps of unblocking.

The aqueous phase is then evaporated under reduced pressure and coevaporated with water. The dinucleoside compound [13] so obtained is directly utilized in the next step.

(c) Unblocking of formyl:

To the dinucleoside [13] dissolved in water, there is added 2 ml of concentrated ammonia. The resulting solution is shaken for one hour at ambient temperature, then evaporated under reduced pressure and coevaporated, with water until complete elimination of ammonia. The resulting dinucleoside [14] is obtained in the form of an ammonium salt.

Purification of the dinucleoside [15].

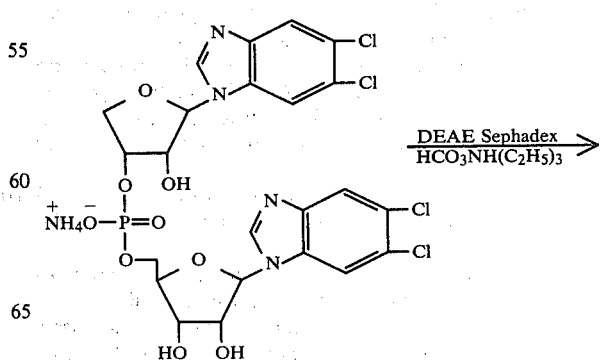

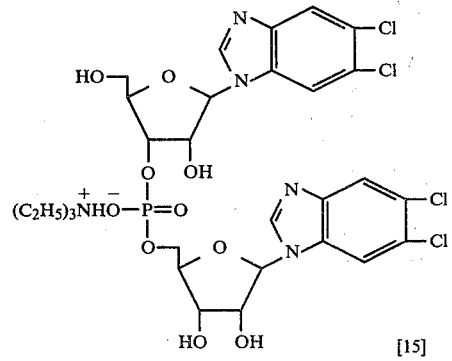

[15]

The dinucleoside [14], is dissolved in a buffer solution (pH 7.50) of triethylammonium hydrogencarbonate (TEAB) $10^{-3}$M, and is chromatographed on an ion exchange resin DEAE-Sephadex A25 form $HCO_3^-$ (30 g, column 25 cm×2.5 ⌀). Elution is made first with a linear gradient TEAB 0.5 m. The fractions corresponding to the target compound [15] are pooled and evaporated under reduced pressure, coevaporated with water, and then lyophilized.

The dinucleoside [15] is obtained in the form of a white powder in a yield of 34% as compared to [11].

The purity of this dinucleoside [15] is controlled by (a) thin layer chromatography RF=0.6 (eluent X), (b) high pressure liquid chromatography, on an analytic water column μ Bondapack $C_{18}$ (25 cm). The gradient of elution is formed from a solution A (2% acetonitrile in an aqueous solution of 1% of ammonium acetate, pH 5.9) and a solution B (40% acetonitrile in an aqueous solution of 1% ammonium acetate, pH 5.9). For a flow rate of 3 ml/mn, elution is made according to a linear gradient from 2% acetonitrile (pure solution A) to 40% acetonitrile (pure solution B) in 15 minutes, followed by a plateau at 40% acetonitrile for 5 minutes.

The base line is controlled by a blank injection, the duration of retention $R_t$ of the dinucleoside [15] is, in such conditions, 13.72 minutes and its spectrometric purity at 254 minutes is better than 99%. This dinucleoside is also identified under the designation of "DDB."

| Eluents Used in Silica (gel = column, plaque: thin layer) Chromatography (V/V): | | |
|---|---|---|
| Eluent I | $CHCl_3$/MeOH = | 9/1 |
| Eluent II | $CHCl_3$/MeOH = | 9.7/0.3 |
| Eluent III | $CH_2Cl_2$/ethyl acetate = | 8.2 |
| Eluent IV | $CH_2Cl_2$/ethyl acetate = | 9.5/05 |
| Eluent V | benzene/MeOH = | 9.8/0.2 |
| Eluent VI | Toluene/MeOH = | 9.93/0.07 |
| Eluent VII | $CHCl_3$/MeOH = | 9.5/05 |
| Eluent VIII | $CH_2Cl_2$/MeOH = | 9.8/02 |
| Eluent IX | $CHCl_2EtOH$ = | 9.85/0.15 |
| Eluent X | Butanol/acetic acid = | 2/1 |

II. The compound of the invention is excellently suitable as an inducing agent for the production of β-interferon.

In order to confirm such utility the following procedures were carried out:

(A) β-Interferon Inducing Properties of Compound [15] (DDB)

(A.1) β-Interferon Production

Thirteen day FS-4 human diploid fibroblast cells are treated for one hour with Poly(I-C) 10 g/ml, with or without DDB or DRB at various concentrations. After one hour the cells are washed, and new medium (without Poly I-C) is added with or without DRB or DDB (Compound [15]). At 6 hours, 30 hours, 54 hours, culture fluids were collected for β-interferon assay, fresh medium with the appropriate concentration of DDB was added. Final culture fluid was collected at 120 hours.

The results are presented in the following table:

TABLE I

| | IFN Units/ml at | | | | TOTAL YIELD |
|---|---|---|---|---|---|
| | 6 hrs | 30 hrs | 54 hrs | 126 hrs | (Units/ml) |
| Poly-(I—C) alone (10 μg/ml: | 960 | 475 | 3 | 1 | 1,439 |
| DRB | | | | | |
| (30.0 μM/ml) | 256 | 190 | 98 | not done | |
| (40.0 μM/ml) | 153 | 1,219 | n.d. | n.d. | |
| (62.5 μM/ml) | 1,280 | 4,400 | 961 | 80 | 6,721 |
| DDB | | | | | |
| (3.75 μM/ml) | 1,280 | 60 | n.d. | n.d. | |
| [15] (12.5 μM/ml) | 3,200 | 4,053 | 605 | <10 | 7,938 |
| (25.0 μM/ml) | 3,840 | 9,600 | 2,520 | 10 | 15,970 |
| (37.4 μM/ml) | 4,480 | 16,215 | 2,240 | 30 | 22,965 |
| (74.86 μM/ml) | 3,840 | 12,800 | 5,440 | 640 | 22,720 |
| (124.77 μM/ml) | 3,400 | 10,027 | 6,700 | 1,920 | 22,074 |

(A.2) β-Interferon Superinduction

Superinduction of diploid fibroblast cells (FS-4) requires utilization of cycloheximide and actinomycin-D after induction with Poly (I-C). DDB (Compound [15]) and DRB at various concentrations are substituted to cycloheximide and actinomycin-D, in the production media at the same time intervals as in the previous experiments, the cells induced are maintained after the superinduction procedure to ascertain their survival. If the inducing agents are cytotoxic, the cells will not survive.

The results are set out in the following Table:

TABLE II

| Results: Superinduction of interferon in FS-4 cells by DDB [15] | | | | | | |
|---|---|---|---|---|---|---|
| | IFN μ/ml at hours | | | | Total IFN | Cell Sur- |
| Inhibitor | 6 | 24 | 48 | 54 | Yield | vival |
| DDB | | | | | | |
| 30 μM/ml | 7,680 | 19,200 | 7,680 | 384 | 34,944 | Yes |
| 60 μM/ml | 5,120 | 25,600 | 5,120 | 1,536 | 37,376 | Yes |
| 120 μM/ml | 5,120 | 12,800 | 15,360 | 2,048 | 35,328 | No |
| DRB | | | | | | |
| 62.5 μM/ml | 480 | 2,400 | 2,560 | 256 | 5,696 | No |
| 125.0 μM/m | 40 | <400 | <40 | <4 | <500 | No |
| Cyclo + Act. D | | | | | 19,200 | No |

(A.3) Repeated Superinduction with DDB

After collecting the IFN-containing media at 54 hours, the first two groups of cultures (DDB 30 and 60 μm/ml) were washed and replenished with growth medium (containing 5% fetal calf serum). Three days later, fresh growth medium was added to these cells. Seven days after the IFN harvest these cultures were re-induced with poly(I).poly(C) and DDB 60 μm/ml. At 48 hours after re-induction the fluids were harvested and assayed for IFN. The yield in both groups (and in a third group of previously uninduced, control cells) was 20,480 μm/ml. Therefore, it is possible to re-induce cultures after DDB superinduction. The high yield of interferon obtained by superinduction with DDB and the possibility of continuous induction permit large scale production of β-interferon with micocarriers in automated fermentors.

(B) Antiviral Properties of Compound [15] (DDB)

When added to viral cultures (in ovo or in mice) at concentrations of from 5 μg/ml, 10 μg/ml, 20 μg/ml, 30 μg/ml, 50 μg/ml, 100 μg/ml, compound [15] is capable of reducing and delaying viral replication, i.e., virustatic and virucidal activity are observed.

(C) Potentialization of the Interferon Activities

When added to cell cultures together with interferon, compound [15] (DDB) protects the cell from vesicular stomatitis virus infections and requires only 10% to 50% of the normal amount of interferon for the same protecting effect.

The novel compound of the invention 5,6-dichloro-1-β-D-ribofuranosyl-1-benzimidazole-3'-yl-5,6-dichloro-1-β-D-ribofuranosyl-1-benzimidazole-5'-yl-phosphate in its free base form or in the form of an acid addition salt thereof can be formulated into therapeutic type compositions by introduction thereof into pyrogen-free saline and in this form is suitable for systemic use.

(D) Immunomodulation and Stimulation of Immune System

In doses ranging from $10^{-8}$ to $10^{-3}$M/l, on natural killer (NK) activity and T-lymphocyte subpopulation in autologous mixed cultures, DDB is able to restore and increase very significantly the number of autologous rosette forming T-lymphocytes, and the NK activity in vitro.

What is claimed is:

1. A compound selected from the group consisting of 5,6-dichloro-1-β-D-ribofuranosyl-1-benzimidazole-3'-yl-5,6-dichloro-1-β-D-ribofuranosyl-1-benzimidazole-5'-yl-phosphate and the pharmaceutically acceptable salts thereof.

2. The compound of claim 1 in the form of its free base having the following formula:

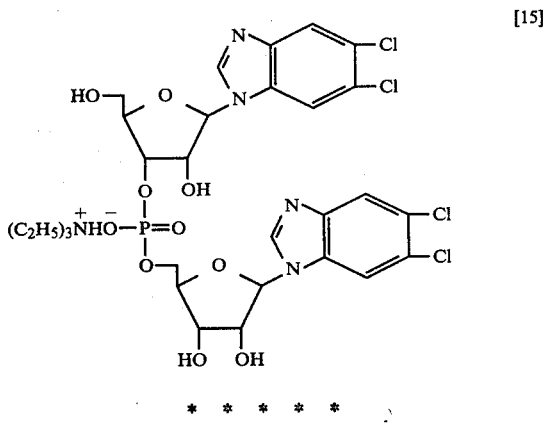

[15]

* * * * *